(12) United States Patent
Gutta et al.

(10) Patent No.: US 6,812,846 B2
(45) Date of Patent: Nov. 2, 2004

(54) SPILL DETECTOR BASED ON MACHINE-IMAGING

(75) Inventors: Srinivas Gutta, Buchanan, NY (US); Vasanth Philomin, Hopewell Junction, NY (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/966,405

(22) Filed: Sep. 28, 2001

(65) Prior Publication Data

US 2003/0063006 A1 Apr. 3, 2003

(51) Int. Cl.[7] .............................................. G08B 21/00
(52) U.S. Cl. ........................ 340/603; 340/604; 340/605
(58) Field of Search ............................... 340/603, 604, 340/605, 905, 990; 250/301, 461.1, 334, 458.1, 459.1; 348/135, 143, 144; 356/73, 301

(56) References Cited

U.S. PATENT DOCUMENTS 3,899,213 A * 8/1975 Fantasia et al. ............. 250/301
5,257,085 A * 10/1993 Ulich et al. ................... 356/73
5,281,826 A * 1/1994 Ivancic et al. ............ 250/461.1
6,008,492 A * 12/1999 Slater et al. ................ 250/334
6,084,510 A * 7/2000 Lemelson et al. .......... 340/539

FOREIGN PATENT DOCUMENTS

JP           7-73384 A  *  3/1995  ........... G08B/17/10

* cited by examiner

*Primary Examiner*—Van T. Trieu
(74) *Attorney, Agent, or Firm*—Gregory L. Thorne

(57) ABSTRACT

Cameras and image processing techniques are applied to the problem of spill detection. Fixed background data may be removed using a technique based on image subtraction. The remainder of one or more images may be segmented. The segments may then be tested to identify and remove from further analysis segments corresponding to non-spill foreground objects, for example by forming luminance and/or chrominance profiles to detect the presence of a high rate of specular albido that would be associated with a wet spill. Further testing may be done, for example by determining if a segment corresponds to a planar object lying in the plane of the floor using planar projection transforms and multiple cameras. If a segment is likely to indicate a spill, a notification may be generated.

20 Claims, 4 Drawing Sheets

SPILL DETECTOR BASED ON MACHINE-IMAGING

BACKGROUND OF THE INVENTION

1. Field of the Invention

The invention relates to spill detectors that employ image-processing techniques to the detection of spills, particularly spills that pose a risk to building occupants such as those that occur when containers are accidentally broken in high traffic areas such as supermarkets or warehouses.

2. Background

Spills of food and other materials in public venues, such as stores, present a serious health hazard. Yet spills occur with some frequency in public places, such as supermarkets, office buildings, commuting stations, etc. The longer a spill remains in a public place, the greater the danger of a serious mishap, such as a slip by an occupant. The delay between the time a spill is detected, reported, and cleaned-up, may be lengthy in most circumstances. Providing sufficient manpower to detect spills quickly is expensive.

Therefore, there is a need in the art for mechanisms for detecting spills that do not rely on human observers and which can notify cleanup personnel quickly so that appropriate action can be taken.

SUMMARY OF THE INVENTION

A spill detector uses optical image-processing hardware and software to identify spills. In an embodiment, one or more cameras capture images and/or video sequences, which are then digitally processed to determine if a spill is evident in the captured scene(s). In embodiments, still images are regularly captured and averaged to create a fixed background image to which a current image may be compared. One or more current images may be segmented and the segments further processed to identify candidate segments identifiable as spills. Segmentation may be performed using known techniques in image analysis and object recognition fields such as region-growing, edge-connecting, or other techniques used for distinguishing fields with homogeneous characteristics such as color, luminance, discrete cosine transform (DCT) profiles, etc. The image(s) is(are) further processed to distinguish candidate spill segments from other segments.

Segments identifiable with the normal stationary background and segments identifiable with non-spill foreground objects, such as people or cars, are preferably removed from the set of candidate segments identifiable with a spill. For example, segments that do not change over time—background segments—may be subtracted, using known object-recognition techniques from the field of image processing aimed at object-recognition. Background subtraction may be used to remove portions of the image before segmentation as well. Segments that move from one image to the next in a current sequence may be identified as non-spill foreground segments. Stereo or multiple camera views may be used to determine the elevation of segments and portions thereof above the floor. Segments that correspond to objects above a range of heights, or ones that are not substantially planar may be removed from the candidate segments.

Candidate segments may be further characterized by luminance and/or chrominance histograms (or "maps") which may be compared to signatures associated with known types of spills. For example, thin runny liquids spills have a high proportion of specular albido and cereal spills a high proportion of diffuse albido and thus correspond to particular luminance maps that may be substantially different from the background or typical non-spill foreground objects.

Where respective cameras form multiple images from different perspectives, the three-dimensional surface shape of segments may be tested to determine if they are planar, as are most hazardous spills such as runny liquids. Thus, a segment in one camera's image may be warped to fit the expected projection of a flat surface, located at the level of the floor, in the other camera's field of view. The segments of the other camera and the predicted segment may then be compared in terms of boundaries, luminance and chrominance maps, and other characteristics to determine if the segments are the same flat floor-level object.

Yet another filtering technique may be to identify occupants and observe avoidance behavior. In other words, occupants would be expected to avoid spills they encounter. Foreground objects may be identified as travelling occupants using known techniques for example as used for occupant-counting. Candidate spill objects may be tested by evaluating observed movement, such as movement that is apparently to avoid the candidate object. Other sources of information may also be used to discount the measure of reliability of the spill detection. For example, the sound of glass breaking or a crashing sound associated with a spill may be recognized by an audio signature and correlated with the above-discussed image/video features. Infrared imaging may be used to identify wet surfaces of spills that are cooled below the ambient temperature by evaporation. Chemical sniffers may detect the presence of certain chemicals in the air, as a result of a spill, to augment the reliability of detection.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE PREFERRED EMBODIMENTS

Figure 1:
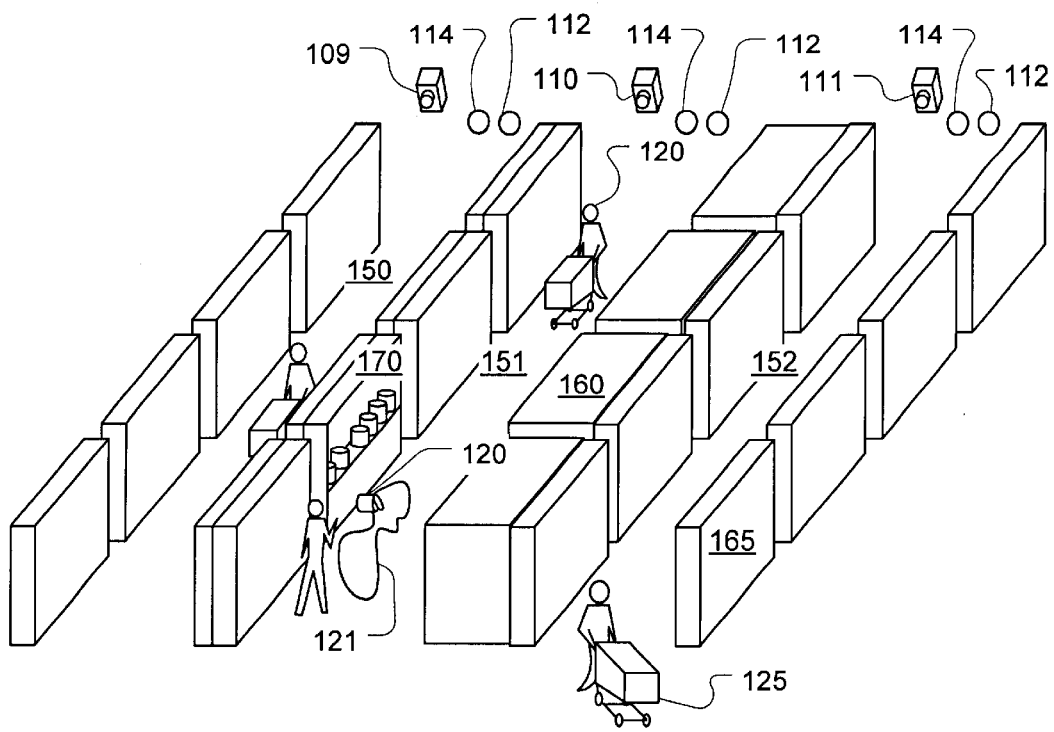
FIG. 1 is an illustration of a context in which an embodiment of the invention may be applied.

Referring to FIG. 1, a public place such as a supermarket, hardware store, or warehouse has traffic areas 150, 151, and 152 between a plurality of storage units 160 and 165 containing goods. The present embodiment is suggestive of a supermarket with some occupants 120 pushing carts. Cameras 109, 110, and 111 are located to view each occupied area 150–152 in which a spill may occur. Other detector devices 112 such as microphones and chemical sniffers may also be located to help detect the respective signatures of spills. Light sources 114 may also be located to illuminate the occupied areas 150–152 and particularly any spills within the occupied areas 150–152.

FIG. 1 illustrates an object 120 that has fallen from a storage unit 170 and spilled its contents creating a spill 121. The spill 121 is in a field of view of camera 110 and therefore defines a portion of an image generated by the camera 110 when illuminated either by ambient light or by the light source 114. The event of the spill may have produced a sound that was picked up by an audio sensor, which may be among the other detector devices 112.

Figure 2:
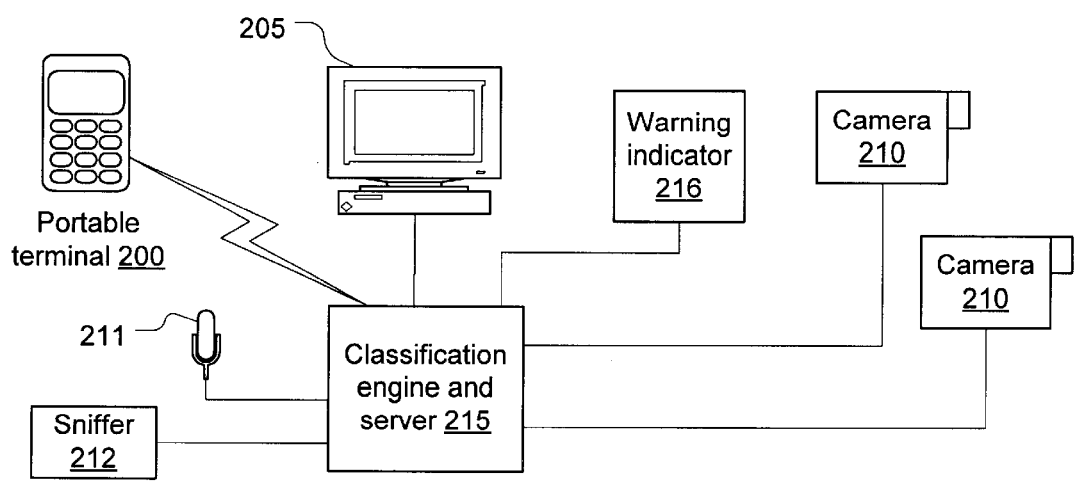
FIG. 2 is a block diagram of digital hardware components for implementing an embodiment of the invention.

Referring now also to FIG. 2, signals from one or more cameras 210 define images that are used by a classification engine and server 215 to identify spills. Signals may also be received from other sources such as one or more microphones 211, chemical sniffers 212, or other devices. The signals may contain identification data that indicates from which device the signals are sent so that the classification engine and server 215 can determine where a spill is located. The classification engine and server 215 determines whether a spill event has occurred and sends appropriate information or alarm signals to fixed 205 or wireless 200 terminals. Personnel who can take appropriate action in the event of a spill may monitor the terminals 205 and/or 200. Warning indicators 216 may also be used to notify occupants of a spill. The warning indicators 216 may be warning flashers located throughout the occupied spaces 150–152 and the one closest to the spill activated in response to the spill. The warning indicators 216 may alternatively include a taped or digital announcement that may indicate the location, type, and other information to occupants as well as maintenance personnel.

Note that the division of function among the components shown in FIG. 2 is merely for purposes of discussion and need not correspond to physically separate components. For example image processing, classification, and server functions may be performed by physically separate components or by a single embedded system. Thus, the layout of FIG. 2 is by no means intended to limit the invention or embodiments in which it is realizable.

Figure 3:
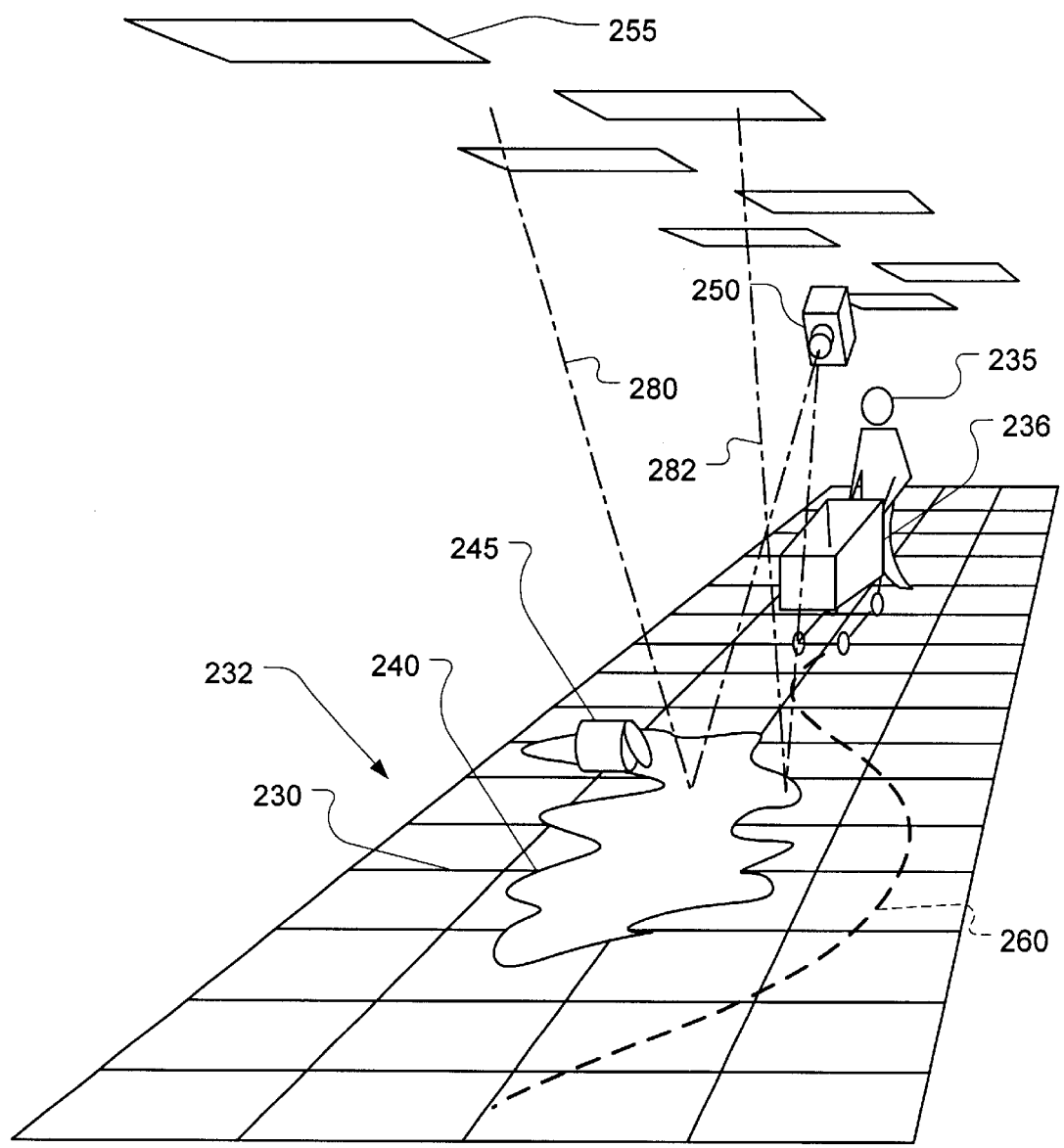
FIG. 3 is an illustration of how an image of a scene containing a spill may be formed using a camera and ambient light.

Referring now also to FIG. 3, a floor surface 232 has a pattern 232 thereon. A spilled container 245 rests on the floor surface 232 and its contents have been expelled creating a spill 240. A camera 250 images the spill 240 along with the adjacent visible portions of the floor surface 232, the container 245, an occupant 235 and cart 236. Ambient lighting is supplied by an array of lights 255. The occupant follows a course indicated by the dashed line 260 to avoid the spill. A sequence of images is generated by the camera 250, which are recorded in the classification engine and server 215. Note that although one camera is shown, more than one camera may be used to image the same scene.

Light reflected from the spill 240 into the camera 250 generates an image area with a defined boundary and characteristic color and luminance features. Preferably, the image is segmented to distinguish the different features of the image. The process of segmenting is a well-known one in image-processing fields, for example it is used in object recognition, character recognition, image indexing, etc. Through segmenting, the image can be broken into portions that may correspond to a spill and portions that are unlikely to correspond to a spill based on various features of each segment. Common techniques for image-segmenting include edge-connecting and region-growing algorithms.

The constant appearance and location of unvarying background features may be used to exclude certain image regions from further analysis. For example, a fixed background image may be subtracted from the current image and the parts that produce a null image may be excluded from segmentation and further analysis. Also, the coordinates of regions of an image that correspond to parts of a scene that are physically unlikely to contain a spill may also be excluded. For example, spills might be unlikely to appear on the tops of storage units 160 and 165.

A spill 240 with a high degree of specular albido will produce a luminance histogram (a histogram plotting luminance signal against the frequency of incidence of the luminance signal in a particular region or the entire image) with a large amount of highlighting. A spill 240 with a high proportion of diffuse albido will produce a luminance histogram with a lower amount of highlighting. When the spill is flat, such as when a runny liquid forms the spill 240, the surface may produce a reflection of objects as does a mirror. Known objects, such as an array of lights supplying ambient illumination may be reflected and recognized in the reflected image. Irregular surfaces may produce strong highlights that would have a specular albido signature in the luminance histogram. Spills may also produce distinct color patterns that may be characterized by chrominance histograms.

The histograms of different segments may be supplied as features to a classification process designed to distinguish the profiles of common non-spill objects (shopping carts, fork-lift trucks, worker uniforms, hair, common clothing, etc.) from common spill objects. The features of an image segment may also be distinguished from the background by comparing their chrominance or luminance histograms with those of background. Highlighting may be very important for spills consisting of clear liquids, for example.

Spills tend to spread, and their corresponding image segments grow, but, when the floor is flat, they tend not to simply translate without growing. Non-spill objects tend to be ones that move without spreading. Using a sequence of images and criteria such as the postulate that spills may spread and/or remain fixed in place while foreground objects such as personnel, occupants, and other objects such as carts, move but do not spread, candidate segments may be further tested. The above may be used as criteria to mark some segments as spills and other segments as non-spill foreground objects. Note that the above criteria are not conclusive because the progressive uncovering of one foreground object by another foreground object will produce a growing region. However, the rate of growing in a succession of images may be used to distinguish spills from progressive uncovering. That is, segments corresponding to spills may grow rapidly and their rate of growth decay quickly. Uncovering may generate growing segments that appear suddenly, grow at a particular rate, and then disappear. These kinds of behaviors of candidate segments may be used to weed out segments corresponding to non-spill foreground objects. A non-spill foreground segment or set of segments may be "removed" from an image by identifying such features, collecting adjacent segments that exhibit them, defining a boundary around them, and removing them from the set of candidate spill segments.

Figure 4:
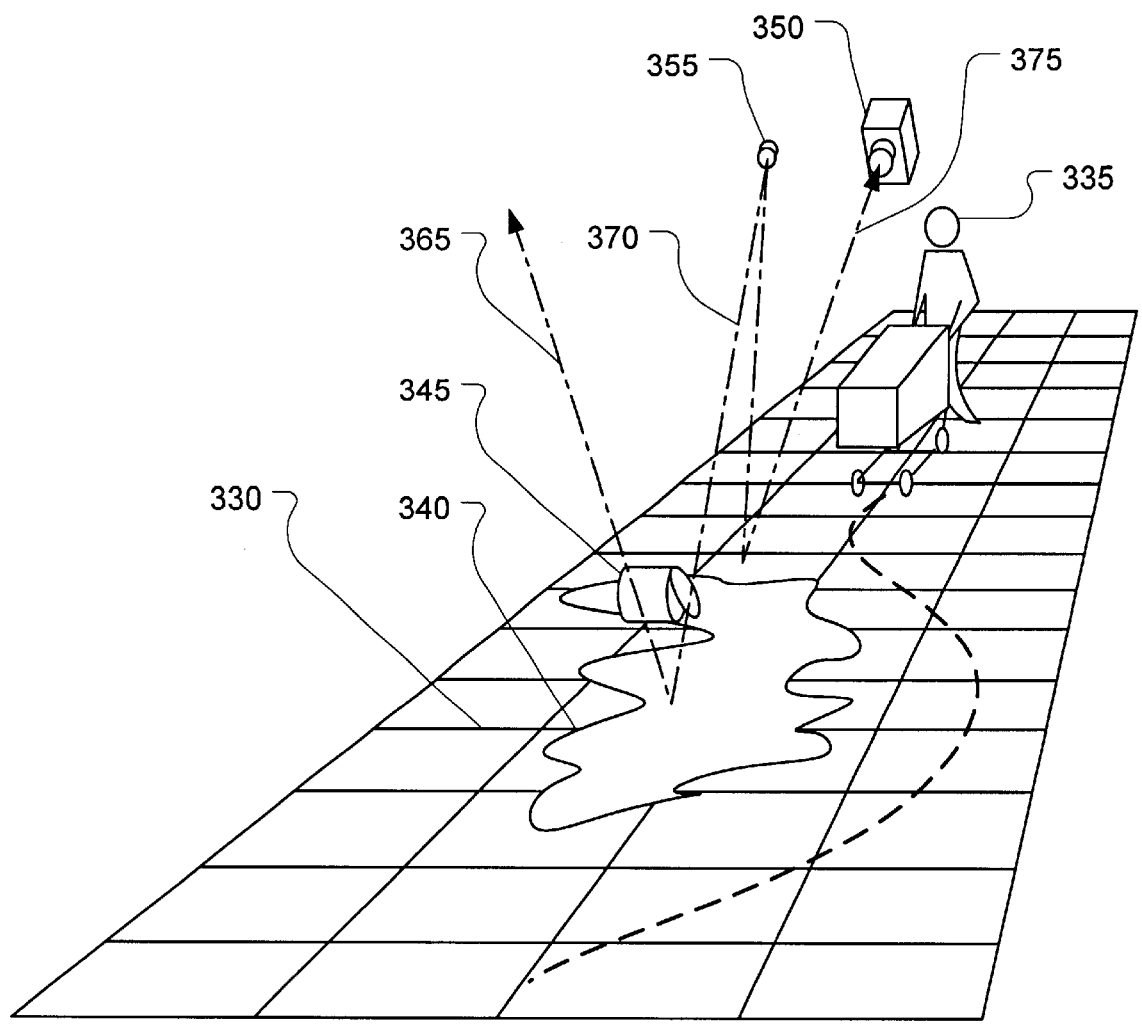
FIG. 4 is an illustration of another way in which an image of a scene containing a spill may be formed using a camera and a light source.

Referring now also to FIG. 4, a light source 355 illuminates the same scene as in FIG. 3. Here the light source may be intermittent such as pulsed and/or scanning laser source, a floodlight, or spotlight. The light from the light source 355 may be of a type designed to reveal spills of certain materials such as an ultraviolet source to stimulate fluorescence or a narrow band source selected for its absorption properties for expected spill materials. The light source 355 may be capable of providing multiple different kinds of light, for example each respective of a different type of spill material.

By using a particular source rather than relying on ambient light, the image of the camera 350 may be more sensitive to wet spills. For example, if the camera is responsive only to infrared light of a certain frequency range and the light source 355 is configured to produce that type of light, then the image will appear to be illuminated only by the light source 355. Illumination of an object by a single source can be particularly useful in probing its reflectance and shape characteristics as is well known to those in the field of object recognition. Here, two ray traces 370 and 375 are shown. These may be among an infinite number of rays or a discrete set generated by a scanning pulsed laser. The trace 370 shows the path of most of the light of ray corresponding to the trace 270 reflecting in specular fashion from the surface of a wet spill 340. The trace 375 shows the path of a substantial fraction of the light from the light source 355 of the corresponding ray reflecting diffusely from the surface of the floor.

Instead of relying on specified spectral properties of the light source 355 and the camera 350, the light from the source 355 could instead be much brighter than other ambient sources. In addition, it could be flashed so that it does not require a great deal of energy or create unneeded light. Each flash could illuminate the scene for a corresponding image. Another alternative is to scan the scene with a pulsed laser.

Referring again to FIG. 1, note that the light source 355 (114 in FIG. 1) may be a spotlight, floodlight, a laser, or a source that produces light with specified frequency profiles that are useful for probing the surfaces in the image. For example, the light source 114 may include an ultraviolet source that causes fluorescence when it illuminates certain types of spilled material. Or it may contain a high proportion of certain spectral components that are particularly-well absorbed by certain dangerous materials so that the camera 110 and light source 114 function as a kind of absorption spectrometer.

The light source may also be a laser scanner that produces intense scan spots on surfaces. Such a scanner could provide a high signal to noise ratio for probing the albido characteristics of the surfaces in question. Certain spills, such as the spill of wet materials such as petroleum chemicals or wet food goods will tend to have a high fraction of spectral albido. Light shined or scanned onto such a surface will return less light than one with a higher fraction of diffuse albido. Providing a large amount of light from a particular source, as is known in the art, may be more useful for determining the albido of a surface than light from many ambient sources because of the blending effect of the latter.

Figure 5:
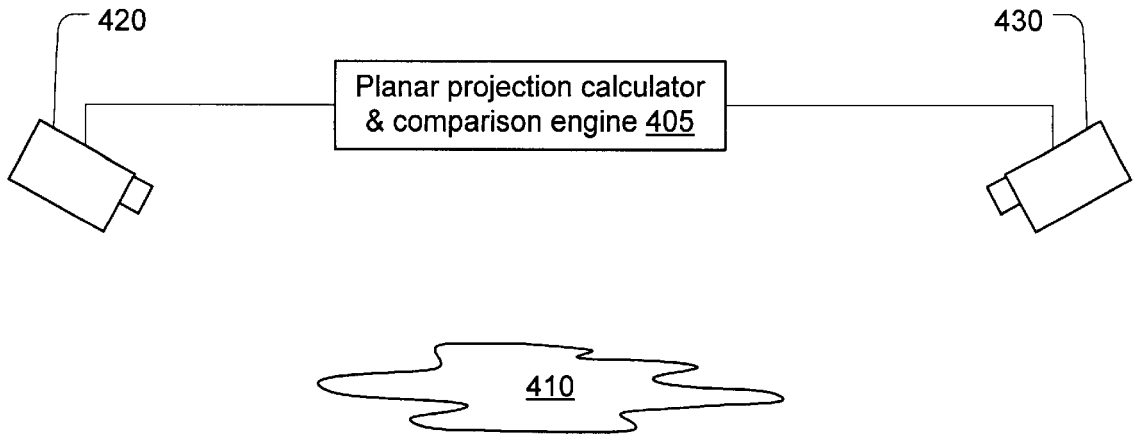
FIG. 5 is an illustration for discussing the use of multiple cameras for obtaining three-dimensional information about a scene containing a spill.

Referring now to FIG. 5, a stereo camera arrangement may be used to gather three-dimensional information about a scene that may be used to test candidate image segments for ones representing leaks. One camera 420 forms one image of a spill 410 and the other camera 430 forms a second image of the same spill 410. The boundary of the shape formed by the spill 410 in the image of the first camera 420 can be morphed into the shape of the image of the spill in the second camera 430 using predefined equations if the camera's positions and orientations are known. Alternatively they can use common reference points in each camera's 420, 430 images to derive a planar projection transform that would morph one spill image into the other. If the morphing works, the spill is in the plane of the floor. If it fails (i.e., the boundaries have different shapes), then the segment does not correspond to the same planar object in the plane of the floor.

Figure 6:
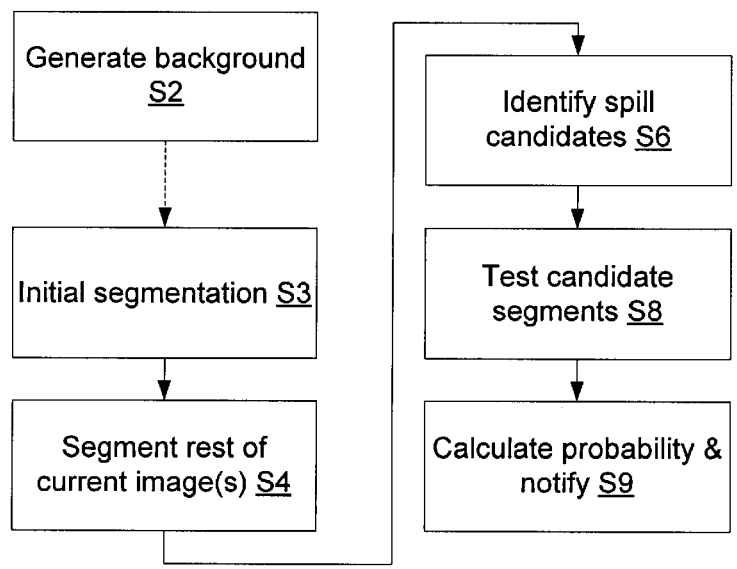
FIG. 6 is an overview flow chart showing how a spill may be identified in a scene according to an embodiment of the invention.

Referring now to FIG. 6, a procedure that may be followed to analyze the data captured by the cameras 210 and other sensors 211 and 212 begins with a process that generates a background image S2. This process may be preformed in advance, at certain times of the day, or continuously. The goal of step S2 is to define a background image that can be subtracted from current images to remove non-changing image segments. An initial step of segmenting is performed in step S3 where parts of the image that will be analyzed are separated from parts that will be ignored. For example, the background data may be removed from current images in step S3 by subtracting the background image from the current image and removing from image portions to be further analyzed those portions that match. On an on-going basis, and optionally in parallel with the process of step S2, current images are segmented in S4 and foreground objects removed.

The image segments may be catalogued and characterized by the various indexes indicating the likelihood that the segment is associated with a spill in step S6. The passing candidate segments are further tested, such as by morphing in separate view images according to a planar transform corresponding to the floor plane. Then the segment or segments having the greatest probability of corresponding to a spill are evaluated against a threshold in step S9 and if one or more passes, action is taken.

Note that the type of tests done in step S3 and S6 are preferably fast simple tests to weed out bad candidate segments without a large computational burden. In principle, such tests are no different in their aim than tests done in step S8, but are separated out only because an intermediate step of filtering out poor candidates may reduce the ultimate computational burden and attendant hardware and energy and requirements for performing the image analyses. Thus, morphing a segment boundary into another segment boundary may be very computationally- and storage-intensive because a large number of boundary vertices may have to be transformed and the calculations involve precise floating point calculations. On the other hand, subtracting the background image can remove a large fraction of the image without heavy computational burden.

The following is a list of possible initial segmenting S3, selection of candidate segments S6, and candidate segment testing S8 processes that may be employed.

Initial segmenting S3.
1. background subtraction
2. The color or luminance of pixels may be used to exclude them from further testing if they are determined in advance not to be possibly associated with a spill. For example, a bright source that saturates the camera's receiver or areas that are completely dark or of a certain hue.
3. The current image may be broken into small pixel block, each of which is subjected to discrete cosine transform (DCT) to measure how "busy" it is. Blocks that are too busy to be usefully segmented may be excluded from further analysis, particularly if it is determined that the types of spills of concern, if any, that would produce high frequency DCT coefficients or of no interest or not dangerous.

Selection of candidate segments S6.

4. Elevation based on stereo views of segment could be calculated to determine if the object is in the plane of the floor.
5. Segments that move in a manner that is indicative of non-spill foreground objects may distinguished. For example, the tops of people's heads would remain substantially constant in area, color and luminance characteristics, and move across the view field with changing size substantially. This behavior is inconsistent with most spills and can be excluded.
6. Color and luminance profiles of segments.
7. Segments that grow at a rate that is consistent with spills.
8. Segment suddenly appears and grows.
9. Segment's appearance coincides with acoustic signal consistent with a spill.

Testing candidate segments S8.

10. Test-warp segment and compare to that of image from another camera.
11. Identify occupants and moving equipment and identify avoidance behavior around candidate segments.
12. Identify non-spill objects by their behavior (e.g., movement without expansion) and aggregate segments corresponding to such objects.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A spill detector, comprising:
    at least one optical imaging device configured to capture at least one image of a scene containing a spill;
    at least one processor having an output and connected to receive the at least one image of a scene from the at least one optical imaging device;
    the at least one processor being configured to identify a spill in the at least one image and generate an indication of event of a spill recognition at the output
    wherein
    the at least one processor is programmed to segment the at least one image and identify a spill responsively to luminance values in a segment of the at least one image.
2. A spill detector as in claim 1, wherein the at least one optical imaging device includes at least one digital camera.
3. A spill detector as in claim 1, wherein
    the at least one processor is programmed to identify a spill responsively to chrominance values in the segment.
4. The spill detector of claim 3, wherein
    the at least one processor is configured to identify the spill by
        creating a profile of at least a segment of the image based on the chrominance values, and
        comparing the profile to characteristics that are indicative of a spill.
5. The spill detector of claim 4, wherein
    the profile includes a histogram of the chrominance values.
6. The spill detector of claim 3, further including:
    a laser that is configured to scan the scene to facilitate identifying the spill.
7. The spill detector of claim 3, wherein
    the profile is created based on a homogeneity of the chrominance values within the segment of the image.
8. The spill detector of claim 3, wherein
    the at least one processor is configured to identify the spill by
        creating a profile of at least a segment of the image based on the luminance and chrominance values, and
        comparing the profile to characteristics that are indicative of a spill.
9. A spill detector as in claim 1, wherein
    the at least one processor is programmed to
        distinguish stationary background features from changing foreground features in the scene and
        identify a spill responsively to portions of the at least one image corresponding to the changing foreground features.
10. The spill detector of claim 1, wherein
    the at least one processor is configured to identify the spill by
        creating a profile of at least a segment of the image based on the luminance values, and
        comparing the profile to characteristics that are indicative of a spill.
11. The spill detector of claim 10, wherein
    the profile includes a histogram of the luminance values.
12. The spill detector of claim 1, further including;
    a laser that is configured to scan the scene to facilitate identifying the spill.
13. The spill detector of claim 1, wherein
    the profile is created based on a homogeneity of the luminance values within the segment of the image.
14. A method of detecting a spill, comprising:
    imaging a scene that may contain a spill to generate an image;
    creating one or more profiles of at least one region of the image according to at least one of chrominance and luminance values;
    comparing the profiles to specified standards for an image of a spill;
    generating a signal indicating a spill responsively to a result of comparing the profiles.
15. A method as in claim 14, wherein
    the imaging includes scanning the scene with a laser.
16. A method as in claim 14, wherein
    the profiling includes
        generating a histogram of the at least one of chrominance and luminance values versus incidence in the at least one region.
17. A method as in claim 14, further comprising
    segmenting according to portions of the image with common contiguous image characteristics, the at least one image region being an image segment resulting from the segmenting.

18. A method of detecting a spill, comprising the steps of:

extracting fixed background data from an image;

segmenting a remainder of the image according to a homogeneity criterion;

testing each segment for properties indicative of a spill;

generating an indication of a spill responsively to a result of the testing.

19. A method as in claim 18, further comprising imaging a scene that may contain a spill with a camera to generate the image.

20. A method as in claim 18, wherein the testing includes generating a histogram of the at least one of chrominance and luminance values versus incidence in the at least region.

* * * * *